United States Patent [19]

Lopes

[11] Patent Number: 5,280,042
[45] Date of Patent: Jan. 18, 1994

[54] DISINFECTING AND SANITIZING COMPOSITIONS

[75] Inventor: John A. Lopes, Troy, Mich.

[73] Assignee: Microcide, Inc., Troy, Mich.

[21] Appl. No.: 888,878

[22] Filed: May 26, 1992

Related U.S. Application Data

[63] Continuation-in-part of Ser. No. 619,245, Nov. 28, 1990, Pat. No. 5,143,720.

[51] Int. Cl.$^5$ ............ C11D 3/48; C11D 7/00; A01N 37/00; A01N 41/10
[52] U.S. Cl. ................ 514/557; 252/106; 429/49; 429/55
[58] Field of Search .............. 252/106; 514/557

[56] References Cited

U.S. PATENT DOCUMENTS

| | | | |
|---|---|---|---|
| 3,431,339 | 3/1969 | Gyarmathy et al. | 424/49 |
| 3,518,343 | 6/1970 | Welsh et al. | 424/44 |
| 3,629,468 | 12/1971 | Anderson | 424/44 |
| 3,772,431 | 11/1973 | Mlkvy et al. | 424/44 |
| 3,888,976 | 6/1975 | Mlkvy et al. | 424/49 |
| 3,919,408 | 11/1975 | Mitchell et al. | 424/49 |
| 3,947,566 | 3/1976 | Sarna | 424/45 |
| 3,962,417 | 6/1976 | Howell | 424/56 |
| 4,088,597 | 5/1978 | Morlock et al. | 424/670 |
| 4,108,981 | 8/1978 | Muhler et al. | 424/49 |
| 4,150,151 | 4/1979 | Pader et al. | 424/49 |
| 4,213,961 | 7/1980 | Curtis et al. | 424/55 |
| 4,256,731 | 3/1981 | Curtis et al. | 424/55 |
| 4,477,438 | 10/1984 | Willcockson et al. | 424/616 |
| 4,545,979 | 10/1985 | Ambike et al. | 424/56 |
| 4,550,018 | 10/1985 | Ambike et al. | 424/56 |
| 4,627,972 | 12/1986 | Gioffre et al. | 424/49 |
| 4,715,980 | 4/1972 | Lopes et al. | 252/106 |
| 4,919,918 | 4/1990 | Cole et al. | 424/49 |
| 4,925,655 | 5/1990 | Smigel et al. | 424/52 |
| 4,945,110 | 7/1990 | Brokken et al. | 514/517 |
| 4,961,923 | 10/1990 | Heyde | 424/55 |
| 4,971,785 | 11/1990 | Wilson et al. | 424/49 |
| 4,980,152 | 12/1990 | Frazier et al. | 424/52 |
| 5,008,106 | 4/1991 | Merianus et al. | 424/80 |
| 5,043,357 | 8/1991 | Hoffler et al. | 514/557 |
| 5,122,541 | 6/1992 | Eggensperger et al. | 514/557 |
| 5,143,720 | 9/1992 | Lopes | 424/55 |

FOREIGN PATENT DOCUMENTS

| | | | |
|---|---|---|---|
| 917432 | 2/1963 | United Kingdom | 424/55 |
| 2216419 | 11/1989 | United Kingdom | 424/55 |

OTHER PUBLICATIONS

C.A. 113: 39166K (TAGAC1) (1989) of JP 01305007 Dec. 8, 1989.
C.A. 107: 6467h (1987)(Adv. Care Health Scope) of JP 62070311, Mar. 31, 1987.
C.A. 107: 46092n(1987) (Sarsunova) of Czech 226096, Jun. 1, 1986.
C.A. 104: 230273m (1986) (Aberg) Gt. Bri. 2163348, Feb. 26, 1986.
C.A. 86: 96010C (1976) (Mordock) Ger. 2527795, Dec. 23, 1976.

*Primary Examiner*—Shep K. Rose
*Attorney, Agent, or Firm*—Krass & Young

[57] ABSTRACT

This invention relates to sanitizing and disinfecting compositions. More particularly, the present invention concerns anhydrous sanitizing and disinfecting concentrate composition suitable for dilution in water to produce aqueous antimicrobial solutions, particularly suited for use as mouthwashes, in human and animal hygiene, and as fresh fruit and vegetable sanitizers, and sanitizers for food processing and other equipment.

1 Claim, No Drawings

DISINFECTING AND SANITIZING COMPOSITIONS

REFERENCE TO RELATED APPLICATION

This application is a continuation-in-part of U.S. patent application Ser. No. 619,245, filed Nov. 28, 1990, now U.S. Pat. No. 5,143,720.

TECHNICAL FIELD

This invention relates to sanitizing and disinfecting compositions. More particularly, the present invention concerns anhydrous sanitizing and disinfecting concentrate composition suitable for dilution in water to produce aqueous antimicrobial solutions, particularly suited for use as mouthwashes, in human and animal hygiene, and as fresh fruit and vegetable sanitizers, and sanitizers for food processing and other equipment.

BACKGROUND OF THE INVENTION

Many sanitizing and disinfecting compositions are known in the art which employ a variety of substances as the active antimicrobial agent. For example, U.S. Pat. No. 4,647,458 to Uemo, et al. discloses mixtures of ethyl alcohol and organic acids as bactericides for food and food processing machinery and utensils. U.S. Pat. No. 3,867,300 to Karabinos, et al. discloses aqueous bactericidal compositions containing an aliphatic onocarboxylic acid of from eight to eleven carbon atoms and a non-ionic or anionic surfactant. British Patent specification 917,432 to Pennwalt Chemicals Corp. discloses sanitizing compositions comprising an alkyl aryl sulfonic acid or salt thereof, together with an acid component to generate a pH of between about pH 1.5 and pH 3.5 upon dilution in water. U.S. Pat. No. 4,404,040 to Wang discloses sanitizing concentrate compositions comprising an aliphatic short chain fatty acid, a hydrotrope or solubilizer for the fatty acid, and an acid to produce a pH between pH 2 and pH 5 when diluted with water. U.S. Pat. No. 4,715,980 to Lopes, et al. discloses concentrated antimicrobial sanitizing compositions for dilution in water comprising a dicorboxylic acid and an acidic component capable of generating a pH below about pH 5 upon dilution.

Aqueous sanitizing and disinfecting compositions which contain an anionic surfactant and an acidic component generally have short shelf lives because most surfactants lack the requisite stability in acidic aqueous solution. It is therefore an object of the present invention to provide sanitizing and disinfecting compositions in stable concentrated form which are suitable for dilution in water or other suitable solvent for use as oral disinfectants and as sanitizing and disinfecting agents which are safe for use as mouthwashes, for human and animal hygiene, and for sanitizing food or food handling and processing equipment.

SUMMARY OF THE INVENTION

The present invention provides sanitizing and disinfecting compositions which have the following advantages: a) shelf-stability while containing acid-unstable anionic surfactants; b) low cost formulation (only concentrated chemical components are used); c) cost savings in transporting and storing the finished formulations (the bulk of water is excluded); d) elimination of the difficulties in preparing concentrated aqueous formulations with ingredients of low aqueous solubility; e) novel nonaqueous formulations for personal hygiene; f) convenience in carrying personal sanitizers; and g) utility for direct use on raw foods. Moreover, the concentrate formulations of the present invention do not have the instability problems associated with concentrated aqueous formulations at low temperatures.

In accordance with the present invention there are provided sanitizing and disinfecting concentrate compositions having excellent shelf life and chemical stability. The concentrates are capable of dilution with water to form an antimicrobial solution, with the concentrate composition comprising, prior to dilution, a) an anionic surfactant present in an amount of from about 0.25 weight percent to about 10.0 weight percent, b) an acidic component, present in an amount effective to produce a pH of below 5.0 upon dilution with water.

In one embodiment, the concentrate compositions of the present invention are in the form of a solid dry composition suitable for dilution with water just prior to use. In another embodiment, the concentrate compositions of this invention are in the form of a liquid mixture in an anhydrous liquid carrier. The acidic component of these compositions may function both to lower the pH upon dilution with water and as the anhydrous liquid carrier for the other components.

In another embodiment, the compositions are either ready to use or in the form of a concentrate for dilution with water to provide a personal care product having antimicrobial and microbicidal properties.

In another embodiment, the compositions provide a product for combatting protozoan infection.

DETAILED DESCRIPTION

The anhydrous sanitizing and/or disinfecting compositions of this invention comprise an anionic surfactant agent and an acidic component, both of which are miscible with water at low concentrations. The compositions preferably are capable of forming, upon dilution with water, an acidic aqueous antimicrobial solution having a pH below about pH 5.0. The compositions exhibit excellent shelf life and have exceptional activity against gram positive and gram negative bacteria such as *E. coli* and *Staph. aueus.*

The compositions may be in a dry, powdered form or, alternatively, in a liquid form in an anhydrous carrier in which the active components of the mixture are miscible. In certain embodiments of the present invention, the acidic component of the compositions serves a dual role as both acidic component and anhydrous carrier. However, regardless of their physical form, the sanitizing and disinfecting compositions of this invention are formulated of ingredients which are readily miscible with water and effective at low concentrations and are thus suitable for easy use by mixing with water just prior to use.

Depending upon the end use for which the compositions of this invention are intended, the compositions may further contain components such as gums, flavoring agents, sweeteners, coloring agents, and inorganic or organic salts. For example, when used as oral rinses or mouthwashes, the sanitizing and disinfecting compositions of the present invention optionally contain sweeteners, colorants, and flavoring agents in addition to the surfactant and acidic components. When used for disinfecting hands, skin or hair, the formulations of the present invention optionally contain emollients or conditioning agents. In formulations containing a nonaqueous carrier, the carrier may provide the emollient and conditioning functions.

The anionic surfactant agent, acidic components, flavoring agents, gums, colorants, sweeteners, and salts utilizable in the compositions of this invention are selected from the class of substances generally regarded as safe (GRAS) or which have been ascribed food additive status as those terms are defined by the United States Food and Drug Administration in the Code of Federal Regulations, Chapter 21 Parts 178, 182 and 184, or which have low toxicity and have been approved for specific uses by the regulatory agencies.

Suitable anionic surfactant materials for use in the compositions of this invention include the ammonium, sodium, potassium, calcium and magnesium salts of
  (a) $C_6$–$C_{18}$ alkyl- and alkenylsulfates;
  (b) $C_6$–$C_{18}$ alkyl- and alkenyl ether sulfates;
  (c) $C_8$–$C_{16}$ alkyl diphenyl ether disulfonates;
  (d) $C_4$–$C_{18}$ fatty acid isethionates;
  (e) $C_6$–$C_{18}$ alkyl- and alkenysulfonates;
  (f) dialkyl- and dialkenyl sulfosuccinates in which the alkyl or alkenyl groups independently contain from six to eighteen carbon atoms;
  (g) alkylbenzenesulfonates in which the alkyl group contain from six to eighteen carbon atoms;
  (h) naphthalenesulfonates;
  (i) alkylnaphthalenesulfonates in which the alkyl group contains from one to six carbon atoms;
  (j) the mono-(n-alkyl) and mono-(n-alkenyl) acyl esters of $C_2$–$C_4$ hydroxylated monocarboxylic acids, in which the alkyl or alkenyl group contains from six to eighteen carbon atoms;
  (k) the mono-(n-alkyl) and mono-(n-alkenyl) acyl esters of $C_2$–$C_4$ hydroxylated dicarboxylic acids, in which the alkyl or alkenyl group contains from six to eighteen carbon atoms;
  (l) the mono-(n-alkyl) and mono-(n-alkenyl) alkyl esters of $C_2$–$C_4$ dicarboxylic acids, in which the alkyl or alkenyl group contains from six to eighteen carbon atoms, and
  (m) $C_4$–$C_{18}$ fatty alcohol sulfoacetates.

By the term "alkyl" as used throughout this specification and the appended claims is meant a monovalent straight or branched chain hydrocarbon radical which can be thought of as derived from a saturated acyclic hydrocarbon by the removal of one hydrogen atom. By the term "alkenyl" is meant a monovalent hydrocarbon radical containing one or more carbon-carbon double bonds, which radical can be thought of as being derived from an unsaturated acyclic hydrocarbon by the removal of one hydrogen atom.

The term, "salt of a mono-(n-alkyl) or mono-(n-alkenyl) acyl ester of $C_2$–$C_4$ hydroxylated monocarboxylic acids" means an ester-salt of a hydroxylated monocarboxylic acid, such as lactic acid, which has been formed by esterification of its hydroxyl function by another acid, and in which its carboxyl function has been converted to a carboxylate salt. An example of such a compound is so-called "octyl lactylate" which is the ester formed by esterifying the hydroxyl group of lactic acid with octanoic acid, and converting the carboxyl function of the lactic acid portion of the resulting ester to the carboxylate salt form.

Similarly, the term, "salt of a mono-(n-alkyl) or mono-(n-alkenyl) acyl ester of $C_2$–$C_4$ hydroxylated dicarboxylic acids" means an ester-salt of a hydroxylated dicarboxylic acid, such as hydroxymalonic acid, which has been formed by esterification of its hydroxyl function by another acid, and in which its two carboxyl functions have been converted to carboxylate salts.

By the term "salt of a mono-(n-alkyl) or mono-(n-alkenyl) alkyl ester of $C_2$–$C_4$ dicarboxylic acids" is meant an ester-salt of dicarboxylic acid, such as succinic acid, which has been formed by esterification by an alcohol at one carboxyl group.

Preferred anionic surfactants for the compositions of the present invention include the ammonium, sodium, and potassium salts of 1,4-dihexyl sulfosuccinic acid; the ammonium, sodium, and potassium salts of dioctylsulfosuccinic acid; the ammonium, sodium, and potassium salts of lauryl sulfuric acid, and octyl lactylate.

Suitable materials for use as the acidic component in the disinfecting and sanitizing compositions of this invention include acetic acid, adipic acid, ascorbic acid, citric acid, dehydroacetic acid, erythorbic acid, fumaric acid, glutaric acid, gluconic acid, hyaluronic acid, hydroxyacetic acid, lactic acid, malic acid, polymerized carboxylic acids comprising polylactic or polylactic-glycolic acids, succinic acid, sulfamic acid, tannic acid, tartaric acid, and mixtures thereof.

Suitable anhydrous solvents or carriers for the compositions of this invention are selected from propylene glycol, acetic acid, hydroxyacetic acid, and propionic acid.

Suitable sweetening agents for use in the compositions of the present invention include aspartame, acesulfame potassium, dextrose, invert sugar, saccharin, sorbitol, and sucrose. Flavoring agents include those well known to practitioners of the pharmaceutical and formulation arts including artificial strawberry, cherry, raspberry, lemon and lime flavorants as well as menthol and ethyl alcohol.

Components may also be included in the solid dry formulations of the present invention to act as sequestering agents or to reduce the cloudiness which might otherwise result when the compositions are dissolved in hard water. Components which may be employed in the compositions of this invention for this purpose include inorganic and organic salts such as sodium acid pyrophosphate and the chlorides, sulfates, citrates, nitrates, acetates, and lactates of potassium, sodium, ammonium, and zinc. For example, sodium sulfate is used in amounts ranging between about 5 and 85 weight percent and zinc sulfate or sodium citrate are used in amounts of about 10 to about 30 weight percent in the dry solid compositions of this invention. While not adhering to any theory to the exclusion of others, it is believed that the sodium sulfate, zinc sulfate, and sodium citrate control cloudiness by controlling the critical micelle concentration of the resulting aqueous solutions. Similarly, sodium acid pyrophosphate is used in the dry solid compositions of this invention in concentrations ranging between about 30 and 50 weight percent. The sodium acid pyrophosphate is believed to act both as a sequestering agent and as an agent to control critical micelle concentration.

The antimicrobial sanitizing and disinfecting compositions of the present invention may be successfully employed in sanitizing and disinfecting food handling equipment and machinery such as that found in kitchens, dairies, breweries, food packing and canning facilities, beverage plants and the like. Moreover, the compositions of this invention can be used to prepare aqueous antimicrobial solutions for the direct sanitizing of foods such as fresh fruits and vegetables. In this embodiment, the acidic component of the formulations may contain compounds such as citric acid, ascorbic acid or erythorbic acid which retard the browning of fresh fruits and vegetables.

When enhanced with flavoring and sweetening agents, the concentrate compositions of this invention can be used to prepare aqueous disinfecting solutions for use as mouth washes and oral rinses. When combined with emollients, conditions agents, perfumes and coloring agents, the compositions of this invention can be diluted either with water or with a suitable non-aqueous diluent for use as antimicrobial preparations for the hair, hands, and skin.

Dry, powdered concentrate compositions of this invention suitable for use in sanitizing and disinfecting food handling and processing equipment as well as in other applications where compatibility with food for human and animal consumption is a prerequisite comprise from between about 0.05 part by weight to about 10 parts by weight anionic surfactant, with the balance comprising an acidic component in salt or free acid form selected from acetic acid, adipic acid, ascorbic acid, citric acid, hydroxyacetic acid, erythorbic acid, fumaric acid, glutaric acid, gluconic acid, lactic acid, malic acid, succinic acid, tannic acid, tartaric acid, dehydroacetic acid, hyaluronic acid, sulfamic acid, poly-lactic acid, polylactic-glycolic acid, and the like, and mixtures thereof.

Anhydrous liquid concentrate sanitizer formulations in accordance with this invention comprise from between about 0.05 weight percent to about 10 weight percent anionic surfactant component, from about 10 weight percent to about 35 weight percent acidic component, with the balance comprising an anhydrous solvent, preferably propylene glycol. The propylene glycol may be replaced by the acidic component, as in the case of glacial acetic acid, or propionic acid. Small amounts, ranging from 0.1 weight percent to about 3 weight percent of a fatty acid of from eight to twelve carbon atoms may also be added to the mixture.

Dry, solid formulations particularly suited for dilution just prior to use as an oral rinse or mouthwash comprise from about 2 weight percent to about 7.5 weight percent of an anionic surfactant, from about 5 weight percent to about 35 weight percent acidic component.

Dry, solid formulations also particularly suited for dilution just prior to use as an oral rinse or mouthwash comprise from about 2 weight percent to about 35 weight percent citric acid, from about 7 weight percent to about 15 weight percent flavoring agent, and from about 2 weight percent to about 90 weight percent sweetener.

Depending upon the end use intended, in general, the concentrate formulations of the present invention are diluted with either water or a suitable non-aqueous diluent such as propylene glycol. Aqueous antimicrobial solutions are prepared, for example, by diluting from 0.01 parts by weight to about 15 parts by weight of the concentrate with sufficient water to make 100 parts of aqueous solution. For use as an oral rinse or mouthwash, between about 0.5 parts by weight to 2 parts by weight of the concentrate mixture are diluted with sufficient water to make 100 parts by weight. In a preferred embodiment, the concentrate may comprise sodium fluoride, preferably at about 0.005 to about 2 weight percent, and/or dehydroacetic acid or its salt at about 0.005 to about 5 weight percent. For use as an antimicrobial solution for sanitizing the surface of fresh fruits and vegetables, between about 0.01 and about 10 parts by weight of the concentrates of the present invention are diluted with sufficient water to make 100 parts by weight. For use as waterless antimicrobial preparations for the hand, hair, or skin, between about 0.01 weight percent and about 20 weight percent of the concentrates of this invention are diluted with sufficient non-aqueous diluent to make 100 parts by weight total. The concentrates can be diluted or mixed with suitable inert ingredients and molded into a bar for use as sanitizing bar soaps. An excess amount of anionic surfactant may be used as a diluent.

When the disinfecting and sanitizing compositions of this invention are diluted with water or other suitable non-aqueous solvents to form the solutions which are used in the various applications described herein, it is preferred that the concentration of tee anionic surfactant component in the diluted solution falls within the range of about 5 to about 750 parts per million.

Within this range of anionic surfactant concentration, the compositions of the present invention produce solutions in water or other suitable non-aqueous solvents having excellent antimicrobial activity against gram negative and gram positive bacteria as evidenced by the data presented below. In addition, the concentrated compositions of the present invention exhibit exceptional chemical stability and shelf life and are convenient to store and transport because of their small volume.

In tests of the stability of the compositions of the present invention, for example, no deterioration of the compositions or loss of antimicrobial activity upon dilution with water was observed even after allowing the concentrate mixtures to stand for periods of up to six months.

In one preferred aspect, the invention also comprises compositions of the kind described having not only excellent antimicrobial activity against gram negative and gram positive bacteria but also microbicidal activity against these bacteria so that the compositions are suitable for personal care, e.g., as skin care products and personal hygiene products such as soap, shampoos, toothpaste, mouthwash, creams, lotions, and the like. Thus, the antimicrobial properties can be used, e.g. in products that are to be applied to the skin with prolonged skin contact while the microbicidal property can be used in products to be applied to the skin with a short skin contact time. These products can be prepared more economically since they do not require either the usual preservative or they use a lesser amount of these preservatives. The products are in the form of a concentrate composition having improved shelf life and stability and being capable of dilution with water to form a personal care aqueous solution. The concentrate composition comprises: a) an anionic surfactant selected from fatty acid isethionate salts and fatty alcohol sulfoacetate salts and being present in an amount of from about 0.005 weight percent to about 5.0 weight percent, based on the total weight of the concentrate composition; and b) an acidic component, present in an amount effective to produce a pH of below pH 5.0 upon dilution with water to make said aqueous solution in which a solution of the anionic surfactant is present in about 10 to about 50,000 parts per million.

Preferably, the anionic surfactant is selected from the group consisting of salts of fatty acid isethionates of formula

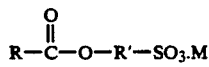

and fatty alcohol sulfoacetates of formula

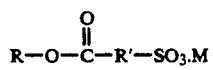

where R is an alkyl or alkenyl group with a chain length of 6 to 16 carbon atoms and R' is an alkyl or alkenyl group with a chain length of up to 4 carbon atoms, and M is a cationic group that forms a salt linkage with a sulfonic acid group, such as the ammonium, sodium, potassium, calcium and magnesium salts.

Preferably, the acidic component is selected from the group consisting of acetic acid, adipic acid, ascorbic acid, citric acid, dehydroacetic acid, erythorbic acid, fumaric acid, glutaric acid, gluconic acid, hyaluronic acid, hydroxyacetic acid, lactic acid, malic acid, succinic acid, sulfamic acid, tannic acid, tartaric acid, and mixtures thereof.

Microbicidal activity, as the term is used herein, is the lethal antimicrobial activity resulting in reduction of the microbial population by a magnitude of five logarithmic units within 30 to 60 seconds.

The preferred sulfonated esters are sodium salts of esters derived from sulfoacetic acid and isethionic acid. Sodium sulfoacetic acid esters are reaction products of a fatty alcohol and sulfoacetic acid. The fatty alcohol of choice has a carbon chain length of 6 to 16. The preferred fatty alcohol ester is a lauryl alcohol ester. A commercially available sodium salt of the ester of sulfoacetic acid, marketed by Stepan Co. under the trade name Lathanol LAL, is especially useful. Sodium isethionic acid esters are reaction products of fatty acids and isethionic acid. The fatty acids of choice used in the present invention are derived from coconut oil with predominant lauric acid (C12), myristic acid (C14), palmitic acid (C16), and oleic acid (C18). The sodium salt of the ester of isethionic acid is commercially available from Rhone Poulenc, American Hoechst corporation and Mazer Chemicals Inc. A preferred salt is the sodium salt of the ester of isethionic acid marketed by Rhone Poulenc under the trade name Igepon AC-78.

The acidulant of the present compositions used to lower the pH for obtaining the desired microbicidal property must be compatible with the anionic surfactants. Suitable acidulants are acetic acid, adipic acid, ascorbic acid, citric acid, dehydroacetic acid, erythorbic acid, fumaric acid, glutaric acid, gluconic acid, hyaluronic acid, hydroxyacetic acid, lactic acid, malic acid, polymerized carboxylic acids comprising polylactic and polylactic-glycolic acid, succinic acid, sulfamic acid, tannic acid, tartaric acid, and mixtures thereof. The compositions can be prepared in the form of a concentrated solid, powder, liquid or gel which can suitably be diluted for direct use as a personal care preparation.

In another preferred aspect, the invention comprises disinfecting and sanitizing compositions useful for preventing protozoal infections. The invention is based on the discovery of a class of anionic agents that under acidic conditions inactivate resistant protozoan forms such as the cysts of Giarbia.

Giardiasis is a waterborne protozoan infection causing an annual worldwide incidence of a half million cases. The infective agent, *Giardia lamblia*, forms resistant cysts that survive for long periods outside the host. Giardia cysts are resistant to soap, dehydration, and stomach acids. They display remarkable resistance to ultra violet radiation. Large outbreaks of waterborne giardiasis are often reported due to the consumption of contaminated tap water as well as untreated water. Contaminated food products, especially raw vegetables, are often the common vehicles of giardiasis. Individuals ca also carry and spread the infective agent on the hands. Outbreaks of giardiasis are often reported in nurseries and other institutions caring for disabled individuals.

Chemicals, now available, that can be used for inactivating Giardia cysts include ozone, chlorine dioxide, elemental iodine, free chlorine, chloramine and quaternary ammonium compounds. However, these chemicals are either unstable, corrosive, highly reactive, and/or toxic. Some of these agents are inconvenient for decontaminating water under field conditions while other agents are unsuitable for decontaminating contaminated raw vegetables. These chemicals are undesirable and inconvenient for hand or skin decontamination.

The present invention provides novel compositions for inactivation of protozoal cysts such as those of Giardia. These compositions can be used for eliminating Giardia from contaminated water, raw vegetables or skin surfaces. These agents can be formulated in stable nonirritating products without the mentioned disadvantages of existing inactivating chemicals.

In a preferred embodiment, the present disinfecting and sanitizing compositions for preventing protozoal infections comprise an acidulant, preferably in an amount effective to produce a pH of below 5.0, and anionic surfactant having biocidal activity against resistant cyst forms and oocyte forms of protozoa, preferably in an amount from about 0.005 weight percent to about 10 weight percent of the composition in use form as when diluted. The acidulant is compatible with the surfactant and preferably is selected from one or more acids of the group consisting of acetic acid, adipic acid, ascorbic acid, citric acid, dehydroacetic acid, erythorbic acid, fumaric acid, glutaric acid, gluconic acid, hyaluronic acid, hydroxyacetic acid, lactic acid, malic acid, polymerized carboxylic acids comprising polylactic and polyglycolic acid, succinic acid, tannic acid, tartaric acid, sulfamic acid, sulfuric acid, phosphoric acid, nitric acid, hydrochloric acid and mixtures thereof. The anionic surfactant is selected from one or more surfactants in free acid or salt form of the group consisting of C6–C18 alkyl- and alkenyl-surfacts; C6–C18 alkyl-and alkenyl-ether sulfates; C8–C16 alkyl diphenyl ether disulfonates; C4–C18 fatty acid isethionates; C6–C18 alkyl- and alkenyl sulfonates; dialyl- and dialkenyl sulfosuccinates in which the alkyl or alkenl groups independently contain from six to eighteen carbon atoms; C6–C18 alkylbenzene sulfonates; naphthalene sulfonates; alkylnaphthalenesulfonates in which the alkyl group contains from one to six carbon atoms; the mono-(n-alkyl) and mono-(n-alkenyl) acyl esters of $C_2$–$C_4$ hydroxylated monocarboxylic acids, in which the alkyl or alkenyl group contains from six to eighteen carbon atoms; the mono-(n-alkyl) and mono-(n-alkenyl) acyl esters of $C_2$–$C_4$ hydroxylated dicarboxylic acids, in which the alkyl or alkenyl group contains from six to eighteen carbon atoms; the mono-(n-alkyl) and mono-(n-alkenyl) acyl esters of $C_2$–$C_4$ dicarboxylic acids, in which the alkyl or alkenyl group contains from six to eighteen carbon atoms; and $C_4$–$C_{18}$ fatty alcohol sulfoacetates. The compositions suitably can be formulated in solid, powder, liquid, lotion or gel form. The compositions preferably are in concentrated stable form so that for use they can be diluted with water or other suitable liquid solvent or diluent to provide a anionic surfactant concentration of about 10 ppm to 50,000 ppm.

Regarding the resistance of protozoal cysts, the cysts of *Giardia muris* approximate *Entamoeba histolytica* cysts in their sensitivity to chlorine. The cysts from *Giardia lamblia*, *Naegleria fowleri*, and *Neggleria gruberi* are one and a half times more sensitive to the lethal action of chlorine. Thus, chemicals which inactivate Giardia offer a greater degree of lethal activity against cysts from other serious pathogens. In particular, the present compositions can be used to inactivate resistant cyst forms of *Entamoeba histolytica*, *Naegleria fowleri*, *Naegleria gruberi*, as well as oocytes of Cryptosporidium. Also contemplated by the present invention is the use of the present compositions as virucidal sanitizing agents against enveloped viruses such as the agents of influenza, herpes, rabies, and AIDS (acquired immunodeficiency syndrome).

The following examples are provided to enable one skilled in the art to practice the invention.

SOLID SANITIZER OR DISINFECTANT FORMULATIONS

The following solid sanitizer/disinfectant formulations were prepared in accordance with the present invention. In each example, the indicated solid dry components were thoroughly mixed to form the solid formulation. For use as a sanitizing or disinfecting solution, the solid formulations were dissolved in water just prior to use.

EXAMPLE 1

| Dry Solid Formulation: | Sodium lauryl sulfate | (6.25 wt %) |
| --- | --- | --- |
| | Anhydrous citric acid | (93.75 wt %) |
| Sanitizing/Disinfecting Solution: | 0.32–0.40 part by weight dry solid formulation | |
| | Water (to make 100 parts by weight) | |

EXAMPLE 2

| Dry Solid Formulation: | Sodium lauryl sulfate | (7.29 wt %) |
| --- | --- | --- |
| | Anhydrous citric acid | (92.71 wt %) |
| Sanitizing/Disinfecting Solution: | 0.343 part by weight dry solid formulation | |
| | Water (to make 100 parts by weight) | |

EXAMPLE 3

| Dry Solid Formulation: | Sodium lauryl sulfate | (5.91 wt %) |
| --- | --- | --- |
| | Anhydrous citric acid | (94.09 wt %) |
| Sanitizing/Disinfecting Solution: | 0.338 part by weight dry solid formulation | |
| | Water (to make 100 parts by weight) | |

EXAMPLE 4

| Dry Solid Formulation: | Sodium lauryl sulfate | (4.50 wt %) |
| --- | --- | --- |
| | Anhydrous citric acid | (95.50 wt %) |
| Sanitizing/Disinfecting Solution: | 0.333 part by weight dry solid formulation | |
| | Water (to make 100 parts by weight) | |

EXAMPLE 5

| Dry Solid Formulation: | Sodium lauryl sulfate | (3.05 wt %) |
| --- | --- | --- |
| | Anhydrous citric acid | (96.95 wt %) |
| Sanitizing/Disinfecting Solution: | 0.328 part by weight dry solid formulation | |
| | Water (to make 100 parts by weight) | |

EXAMPLE 6

| Dry Solid Formulation: | Sodium lauryl sulfate | (6.06 wt %) |
| --- | --- | --- |
| | Anhydrous citric acid | (90.90 wt %) |
| | Undecylenic acid | (3.03 wt %) |
| Sanitizing/Disinfecting Solution: | 0.32–0.40 part by weight dry solid formulation | |
| | Water (to make 100 parts by weight) | |

EXAMPLE 7

| Dry Solid Formulation: | Sodium lauryl sulfate | (6.15 wt %) |
| --- | --- | --- |
| | Anhydrous citric acid | (92.31 wt %) |
| | Decanoic acid | (3.03 wt %) |
| Sanitizing/Disinfecting Solution: | 0.32–0.40 part by weight dry solid formulation | |
| | Water (to make 100 parts by weight) | |

EXAMPLE 8

| Dry Solid Formulation: | Sodium lauryl sulfate | (7.19 wt %) |
| --- | --- | --- |
| | Anhydrous citric acid | (91.90 wt %) |
| | Decanoic acid or lauric acid | (0.99 wt %) |
| Sanitizing/Disinfecting Solution: | 0.40 part by weight dry solid formulation | |
| | Water (to make 100 parts by weight) | |

EXAMPLE 9

| Dry Solid Formulation: | Sodium lauryl sulfate | (0.48 wt %) |
| --- | --- | --- |
| | Anhydrous citric acid | (65.70 wt %) |
| | Sodium citrate | (33.82 wt %) |
| Sanitizing/Disinfecting Solution: | 5.18 part by weight dry solid formulation | |
| | Water (to make 100 parts by weight) | |

EXAMPLE 10

| Dry Solid Formulation: | Sodium lauryl sulfate | (0.48 wt %) |
| --- | --- | --- |
| | Anhydrous citric acid | (65.07 wt %) |
| | Dehydroacetic acid | (0.95 wt %) |
| | Sodium citrate | (33.49 wt %) |
| Sanitizing/Disinfecting Solution: | 5.23 part by weight dry solid formulation | |
| | Water (to make 100 parts by weight) | |

EXAMPLE 11

| Dry Solid | Dioctyl sulfosuccinic | (3.4 wt %) |
| --- | --- | --- |

-continued

| Formulation: | acid | |
| --- | --- | --- |
| | Lactic acid | (96.60 wt %) |
| Sanitizing/Disinfecting Solution: | 0.88 part by weight dry solid formulation | |
| | Water (to make 100 parts by weight) | |

EXAMPLE 12

| Dry Solid Formulation: | Octyl lactylate (Paniplus) | (3.4 wt %) |
| --- | --- | --- |
| | Lactic acid | (96.6 wt %) |
| Sanitizing/Disinfecting Solution: | 0.88 part by weight dry solid formulation | |
| | Water (to make 100 parts by weight) | |

EXAMPLE —

| Dry Solid Formulation: | Octyl lactylate (Paniplus) | (1.7 wt %) |
| --- | --- | --- |
| | Dioctyl sulfosuccinic acid | (1.7 wt %) |
| | Lactic acid | (96.6 wt %) |
| Sanitizing/Disinfecting Solution: | 0.88 part by weight dry solid formulation | |
| | Water (to make 100 parts by weight) | |

The sanitizing and disinfecting efficacy of the dilute aqueous solutions of the dry formulations of Example 2-5 above was evaluated using the procedure of Method No. 6 from the 13th Edition of the *Official Methods of Analysis of the A. O. A. C.*, 1111 North 19th Street, Alexandria, Va. 22209.

A concentrated suspension of *Staphylococcus aureus* or *Escherichia coli* was contacted with the reconstituted aqueous solutions of sanitizer/disinfectant from each example and aliquot samples were withdrawn after 30 and 60 seconds. These aliquot samples were plated on appropriate nutrient media, cultured and the resulting bacterial colonies counted to determine the number of surviving bacteria per milliliter. The results of these tests appear in Table 1.

TABLE 1
MICROBIOLOGICAL EFFICACY OF RECONSTITUTED AQUEOUS SOLUTIONS OF SOLID SANITIZER/ DISINFECTANT FORMULATIONS OF THE INVENTION

| | | | | Number of Bacteria/mL | |
| --- | --- | --- | --- | --- | --- |
| Example | Test | Bacterial Species | Initially | After 30 sec. | After 60 sec. |
| 2 | 1 | Staphylococcus aureus | $77 \times 10^6$ | 1 | 0 |
| 2 | 2 | Staphylococcus aureus | $77 \times 10^6$ | 1 | 0 |
| 2 | 3 | Escherichia coli | $79 \times 10^6$ | 0 | 0 |
| 2 | 4 | Escherichia coli | $79 \times 10^6$ | 0 | 0 |
| 3 | 1 | Staphylococcus aureus | $77 \times 10^6$ | 5 | 0 |
| 3 | 2 | Staphylococcus aureus | $77 \times 10^6$ | 7 | 0 |
| 3 | 3 | Escherichia coli | $79 \times 10^6$ | 0 | 0 |
| 3 | 4 | Escherichia coli | $79 \times 10^6$ | 0 | 0 |
| 4 | 1 | Staphylococcus aureus | $77 \times 10^6$ | 19 | 1 |
| 4 | 2 | Staphylococcus aureus | $77 \times 10^6$ | 16 | 0 |
| 4 | 3 | Escherichia coli | $79 \times 10^6$ | 1 | 0 |
| 4 | 4 | Escherichia coli | $79 \times 10^6$ | 1 | 0 |
| 5 | 1 | Staphylococcus aureus | $77 \times 10^6$ | 105 | 3 |
| 5 | 2 | Staphylococcus aureus | $77 \times 10^6$ | 98 | 7 |
| 5 | 3 | Escherichia coli | $79 \times 10^6$ | 60 | 38 |
| 6 | 4 | Escherichia coli | $79 \times 10^6$ | 51 | 35 |

SOLID ORAL RINSE OR MOUTH WASH FORMULATION

Several solid oral rinse or mouth wash concentrate formulations were prepared in accordance with the present invention by thoroughly mixing the components indicated in each of the following examples. For use as an oral rinse or mouth wash, the solid formulations were dissolved in water just prior to use.

EXAMPLE 14

| Dry Solid Formulation: | Sodium lauryl sulfate | (2.5 wt %) |
| --- | --- | --- |
| | Anhydrous citric acid | (31.6 wt %) |
| | Saccharin | (1.5 wt %) |
| | FD&C Blue #1 powder | (0.2 wt %) |
| | Peppermint flavor powder | (5 wt %) |
| | Menthol | (4 wt %) |
| | Sorbitol | (55.2 wt %) |
| Oral rinse/mouth wash Solution: | 1 part by weight dry solid formulation | |
| | Water (to make 100 parts by weight) | |

EXAMPLE 15

| Dry Solid Formulation: | Sodium lauryl sulfate | (2.5 wt %) |
| --- | --- | --- |
| | Anhydrous citric acid | (31.6 wt %) |
| | Saccharin | (1.5 wt %) |
| | FD&C Red #40 powder | (0.4 wt %) |
| | Raspberry flavor powder | (8 wt %) |
| | Menthol | (2 wt %) |
| | Sorbitol | (54 wt %) |
| Oral rinse/mouth wash Solution: | 1 part by weight dry solid formulation | |
| | Water (to make 100 parts by weight) | |

EXAMPLE 16

| Dry Solid Formulation: | Sodium lauryl sulfate | (2.5 wt %) |
| --- | --- | --- |
| | Anhydrous citric acid | (31.6 wt %) |
| | Saccharin | (1.5 wt %) |
| | FD&C Red #40 powder | (0.4 wt %) |
| | Raspberry flavor powder | (8 wt %) |
| | Menthol | (2 wt %) |
| | $ZnSO_4.7H_2O$ | (30 wt %) |
| | Sorbitol | (24 wt %) |
| Oral rinse/mouth wash Solution: | 1 part by weight dry solid formulation | |
| | Water (to make 100 parts by weight) | |

EXAMPLE 17

| Dry Solid | Sodium lauryl sulfate | (2.5 wt %) |
| --- | --- | --- |

-continued

| Formulation: | Anhydrous citric acid | (31.6 wt %) |
| --- | --- | --- |
| | Saccharin | (1.5 wt %) |
| | FD&C Red #40 powder | (0.4 wt %) |
| | Raspberry flavor powder | (8 wt %) |
| | Menthol | (2 wt %) |
| | Sodium citrate | (10 wt %) |
| | ZnSo$_4$.7H$_2$O | (20 wt %) |
| | NaF | (5 wt %) |
| | Sorbitol | (19 wt %) |
| Oral rinse/ | 1 part by weight dry solid formulation | |
| mouth wash Solution: | Water (to make 100 parts by weight) | |

EXAMPLE 17A

| Liquid Concentrated Mouth Wash | |
| --- | --- |
| Ingredients | Percentage |
| Sodium Lauryl Sulfate | 3.62 |
| Citric Acid (Unhydrous powder) | 18.91 |
| K-ACESULFAME (Sweetener) | 8.43 |
| FD&C Blue #1 | 0.02 |
| FD&C Yellow #5 | 0.02 |
| Menthol | 3.61 |
| Mint Flavor (powder) | 18.07 |
| Propylene glycol | 47.32 |
| Total Weight | 100.00 |

For use 0.8303 grams of the liquid concentrate is made up to 100 ml with water to reconstitute aqueous mouth wash.

EXAMPLE 17B

| Aqueous Mouth Wash With Sodium Fluoride and Dehydroacetic Acid | | |
| --- | --- | --- |
| Ingredients | Use Solution | Solid (Conc.) |
| Sodium Lauryl Sulfate | 0.03 | 2.13 |
| Citric Acid (Unhydrous powder) | 0.157 | 11.18 |
| K-ACESULFAME (SUNNETTE) | 0.07 | 5.00 |
| FD&C Blue #1 | 0.0002 | 0.015 |
| FD&C Yellow #5 | 0.0002 | 0.015 |
| Menthol | 0.03 | 2.13 |
| Zinc Sulfate Monohydrate | 0.157 | 11.18 |
| Mint Flavor (powder) | 0.15 | 10.68 |
| Sodium Sulfate (Unhydrous pwdr) | 0.74 | 52.69 |
| Sodium Fluoride | 0.02 | 1.42 |
| DEHYDROACETIC ACID | 0.05 | 3.56 |
| Dry weight | 1.4044 | 100.00 |
| Water | 100.0 | 0.0 |

For use 1.4044 gm is dissolved in 100 ml of tap or natural drinking water. The resulting mouth wash is a clear transparent solution without the need to add alcohol to achieve clarity.

EXAMPLE 17C

| Aqueous Mouth Wash With Chlorophyllin | | |
| --- | --- | --- |
| Ingredients | Use Solution | Solid (Conc.) |
| Sorbitol | 10.00 | 88.74 |
| Sodium sulfate | 0.74 | 6.57 |
| Citric acid | 0.157 | 1.39 |
| Zinc sulfate | 0.157 | 1.39 |
| Flavor | 0.15 | 1.33 |
| Menthol | 0.03 | 0.27 |
| Sodium lauryl sulfate | 0.03 | 0.27 |
| Chlorophyllin | 0.004 | 0.04 |
| Dry Weight | 11.268 | 100.00 |
| Water | 100.0 | 0.0 |

For use dissolve 11.268 gm in 100 ml of tap water or natural drinking water. The resulting mouth wash is a clear transparent solution without the need to add alcohol for clarity.

EXAMPLE 17D

| Aqueous Mouth Wash With Chlorophyllin | | |
| --- | --- | --- |
| Ingredients | Use Solution | Solid (Conc.) |
| Sorbitol | 5.00 | 79.79 |
| Sodium sulfate | 0.74 | 11.80 |
| Citric acid | 0.157 | 2.50 |
| Zinc sulfate | 0.157 | 2.50 |
| Flavor | 0.15 | 2.39 |
| Menthol | 0.03 | 0.48 |
| Sodium lauryl sulfate | 0.03 | 0.48 |
| Chlorophyllin | 0.004 | 0.06 |
| Dry weight | 11.268 | 100.00 |
| Water | 100.0 | 0.0 |

For use dissolve 6.268 gm in 100 ml of tap or natural drinking water. The resulting mouth wash is a clear transparent solution without the need to add alcohol for clarity.

EXAMPLE 17E

| Aqueous Mouth Wash With Alcohol | |
| --- | --- |
| Ingredients | Percentage w/v |
| Sodium lauryl sulfate | 0.03 |
| Citric acid | 0.1 |
| Ascorbic acid | 0.1 |
| Sorbitol | 2.0 |
| Sodium sulfate | 0.74 |
| Zinc sulfate | 0.157 |
| Flavor | 0.15 |
| Acesulfame-K (Sunnete) | 0.07 |
| Menthol | 0.03 |
| Chlorophyllin | 0.004 |
| Alcohol | 5.0 |
| Water to make volume to | 100 ml |

EXAMPLE 17F

| Aqueous Mouth Wash With Alcohol | |
| --- | --- |
| Ingredients | Percentage w/v |
| Sodium lauryl sulfate | 0.03 |
| Citric acid | 0.1 |
| Ascorbic acid | 0.1 |
| Sorbitol | 2.0 |
| Sodium sulfate | 0.74 |
| Zinc sulfate | 0.157 |
| Flavor | 0.15 |
| Acesulfame-K (Sunnete) | 0.07 |
| Menthol | 0.03 |
| Color | 0.004 |
| Alcohol | 10.0 |
| Water to make volume to | 100 ml |

The antimicrobial efficacy of the reconstituted aqueous solutions of the dry oral rinse or mouth wash formulations of Examples 15-17 above was evaluated using the procedure of Method No. 6 from the 13th Edition of the *Official Methods of Analysis of the A. O. A. C.*, 111 North 19th Street, Alexandria, Va. 22209 described above. The results of these tests appear in Table 2.

TABLE 2

MICROBIOLOGICAL EFFICACY OF RECONSTITUTED AQUEOUS SOLUTIONS OF SOLID ORAL RINSE/MOUTH WASH FORMULATIONS OF THE INVENTION

| Example | Test | Bacterial Species | Initially | After 30 sec. | After 60 sec. |
|---|---|---|---|---|---|
| 15 | 1 | *Staphylococcus aureus* | $77 \times 10^6$ | 0 | 0 |
| 15 | 2 | *Staphylococcus aureus* | $77 \times 10^6$ | 0 | 0 |
| 15 | 3 | *Escherichia coli* | $79 \times 10^6$ | 0 | 0 |
| 15 | 4 | *Escherichia coli* | $79 \times 10^6$ | 0 | 0 |
| 16 | 1 | *Staphylococcus aureus* | $77 \times 10^6$ | 0 | 0 |
| 16 | 2 | *Staphylococcus aureus* | $77 \times 10^6$ | 0 | 0 |
| 16 | 3 | *Escherichia coli* | $79 \times 10^6$ | 0 | 0 |
| 16 | 4 | *Escherichia coli* | $79 \times 10^6$ | 0 | 0 |
| 17 | 1 | *Staphylococcus aureus* | $77 \times 10^6$ | 1 | 0 |
| 17 | 2 | *Staphylococcus aureus* | $77 \times 10^6$ | 0 | 0 |
| 17 | 3 | *Escherichia coli* | $79 \times 10^6$ | 0 | 0 |
| 17 | 4 | *Escherichia coli* | $79 \times 10^6$ | 0 | 0 |

ANHYDROUS LIQUID SANITIZER OR DISINFECTANT FORMULATIONS

The following anhydrous liquid sanitizer/disinfectant formulations in accordance with the present invention were prepared by thoroughly dissolving the indicated solid components in the indicated liquid component (s) to form an anhydrous sanitizer or disinfectant formulation. In Examples 18-22, the solid components were dissolved in propylene glycol as the solvent and had a solid acidic component. In Examples 20-26, the acidic component itself was liquid and served the dual function of solvent and acidic component. For use as a sanitizing or disinfecting solution, the liquid formulations were dissolved in water just prior to use at the concentrations indicated.

EXAMPLE 18

| Anhydrous Liquid Formulation: | Sodium lauryl sulfate | (3.0 wt %) |
|---|---|---|
| | Anhydrous citric acid | (29.0 wt %) |
| | Propylene glycol | (68.0 wt %) |
| Sanitizing/Disinfecting Solution: | 1.0 part by weight liquid formulation Water (to make 100 parts by weight) | |

EXAMPLE 19

| Anhydrous Liquid Formulation: | Sodium lauryl sulfate | (4.0 wt %) |
|---|---|---|
| | Anhydrous citric acid | (29.0 wt %) |
| | Propylene glycol | (66.0 wt %) |
| | Octanoic/decanoic acid mixture (Emery 6358) | (1.0 wt %) |
| Sanitizing/Disinfecting Solution: | 1.0 part by weight liquid formulation Water (to make 100 parts by weight) | |

EXAMPLE 20

| Anhydrous Liquid Formulation: | Sodium lauryl sulfate | (4.0 wt %) |
|---|---|---|
| | Anhydrous citric acid | (29.0 wt %) |
| | Propylene glycol | (66.0 wt %) |
| | Decanoic acid | (1.0 wt %) |
| Sanitizing/Disinfecting Solution: | 1.0 part by weight liquid formulation Water (to make 100 parts by weight) | |

EXAMPLE 21

| Anhydrous Liquid Formulation: | Sodium lauryl sulfate | (4.0 wt %) |
|---|---|---|
| | Anhydrous citric acid | (29.0 wt %) |
| | Propylene glycol | (66.0 wt %) |
| | Undecylenic acid | (1.0 wt %) |
| Sanitizing/Disinfecting Solution: | 1.0 part by weight liquid formulation Water (to make 100 parts by weight) | |

EXAMPLE 22

| Anhydrous Liquid Formulation: | Sulfosuccinic acid, dioctyl ester | (4.0 wt %) |
|---|---|---|
| | Anhydrous citric acid | (29.0 wt %) |
| | Propylene glycol | (67.0 wt %) |
| Sanitizing/Disinfecting Solution: | 1.0 part by weight liquid formulation Water (to make 100 parts by weight) | |

EXAMPLE 23

| Anhydrous Liquid Formulation: | Dioctyl sulfosuccinic acid | (3.0 wt %) |
|---|---|---|
| | Glacial acetic acid | (97.0 wt %) |
| Sanitizing/Disinfecting Solution: | 1.0 part by weight liquid formulation Water (to make 100 parts by weight) | |

EXAMPLE 24

| Anhydrous Liquid Formulation: | Octyl lactylate (Paniplus) | (1.5 wt %) |
|---|---|---|
| | Dioctyl sulfosuccinic acid | (1.5 wt %) |
| | Glacial acetic acid | (97.0 wt %) |
| Sanitizing/Disinfecting Solution: | 1.0 part by weight liquid formulation Water (to make 100 parts by weight) | |

EXAMPLE 25

| Anhydrous Liquid Formulation: | Octyl lactylate (Paniplus) | (3.0 wt %) |
|---|---|---|
| | Glacial acetic acid | (97.0 wt %) |
| Sanitizing/Disinfecting Solution: | 1.0 part by weight liquid formulation Water (to make 100 parts by weight) | |

EXAMPLE 26

| Anhydrous Liquid Formulation: | Octyl lactylate (Paniplus) | (3.0 wt %) |
|---|---|---|
| | Dehydroacetic acid | (5.0 wt %) |
| | Glacial acetic acid | (92.0 wt %) |
| Sanitizing/Disinfecting Solution: | 1.0 part by weight liquid formulation Water (to make 100 parts by weight) | |

SOLID SALAD FRESHENER/SANITIZER FORMULATIONS

EXAMPLE 27

| Dry Solid | Sodium lauryl sulfate | (1.79 wt %) |
|---|---|---|

-continued

| Formulation: | Anhydrous citric acid | (26.78 wt %) |
| | Ascorbic acid | (71.43 wt %) |
| Sanitizing/Dis-infecting Solution: | 1.4 parts by weight dry solid formulation | |
| | Water (to make 100 parts by weight) | |

EXAMPLE 28

| Dry Solid Formulation: | Sodium lauryl sulfate | (1.79 wt %) |
| | Anhydrous citric acid | (26.78 wt %) |
| | Erythorbic acid | (71.43 wt %) |
| Sanitizing/Dis-infecting Solution: | 1.4 parts by weight dry solid formulation | |
| | Water (to make 100 parts by weight) | |

EXAMPLE 29

| Dry Solid Formulation: | Sodium lauryl sulfate | (0.46 wt %) |
| | Anhydrous citric acid | (6.95 wt %) |
| | Ascorbic acid | (92.59 wt %) |
| Sanitizing/Dis-infecting Solution: | 5.4 parts by weight dry solid formulation | |
| | Water (to make 100 parts by weight) | |

EXAMPLE 30

| Dry Solid Formulation: | Sodium lauryl sulfate | (0.46 wt %) |
| | Anhydrous citric acid | (6.95 wt %) |
| | Erythorbic acid | (92.59 wt %) |
| Sanitizing/Dis-infecting Solution: | 5.4 parts by weight dry solid formulation | |
| | Water (to make 100 parts by weight) | |

EXAMPLE 31

| Dry Solid Formulation: | Sodium lauryl sulfate | (0.95 wt %) |
| | Ascorbic acid | (38.09 wt %) |
| | Sodium sulfate | (60.95 wt %) |
| Sanitizing/Dis-infecting Solution: | 2.63 parts by weight dry solid formulation | |
| | Water (to make 100 parts by weight) | |

EXAMPLE 32

| Dry Solid Formulation: | Sodium lauryl sulfate | (0.95 wt %) |
| | Erythorbic acid | (38.09 wt %) |
| | Sodium sulfate | (60.95 wt %) |
| Sanitizing/Dis-infecting Solution: | 2.63 parts by weight dry solid formulation | |
| | Water (to make 100 parts by weight) | |

EXAMPLE 33

| Dry Solid Formulation: | Sodium lauryl sulfate | (0.85 wt %) |
| | Citric acid | (10.82 wt %) |
| | Ascorbic acid | (33.97 wt %) |
| | Sodium sulfate | (54.35 wt %) |
| Sanitizing/Dis-infecting Solution: | 2.94 parts by weight dry solid formulation | |
| | Water (to make 100 parts by weight) | |

EXAMPLE 34

| Dry Solid Formulation: | Sodium lauryl sulfate | (0.85 wt %) |
| | Citric acid | (10.82 wt %) |
| | Erythorbic acid | (33.97 wt %) |
| | Sodium sulfate | (54.35 wt %) |
| Sanitizing/Dis-infecting Solution: | 2.94 parts by weight dry solid formulation | |
| | Water (to make 100 parts by weight) | |

EXAMPLE 35

| Dry Solid Formulation: | Sodium lauryl sulfate | (1.06 wt %) |
| | Citric acid | (13.54 wt %) |
| | Ascorbic acid | (42.60 wt %) |
| | Lauric acid | (0.17 wt %) |
| | Sodium acid pyrophosphate | (42.60 wt %) |
| Sanitizing/Dis-infecting Solution: | 2.35 parts by weight dry solid formulation | |
| | Water (to make 100 parts by weight) | |

EXAMPLE 36

| Dry Solid Formulation: | Sodium lauryl sulfate | (1.06 wt %) |
| | Citric acid | (13.54 wt %) |
| | Erythorbic acid | (42.60 wt %) |
| | Lauric acid | (0.17 wt %) |
| | Sodium acid pyrophosphate | (42.60 wt %) |
| Sanitizing/Dis-infecting Solution: | 2.35 parts by weight dry solid formulation | |
| | Water (to make 100 parts by weight) | |

EXAMPLE 37

| Dry Solid Formulation: | Sodium lauryl sulfate | (1.85 wt %) |
| | Citric acid | (23.60 wt %) |
| | Ascorbic acid | (74.23 wt %) |
| | Lauric acid | (0.29 wt %) |
| Sanitizing/Disinfecting Solution: | 1.35 parts by weight dry solid formulation | |
| | Water (to make 100 parts by weight) | |

EXAMPLE 38

| Dry Solid Formulation: | Sodium lauryl sulfate | (1.85 wt %) |
| | Citric acid | (23.60 wt %) |
| | Erythorbic acid | (74.23 wt %) |
| | Lauric acid | (0.29 wt %) |
| Sanitizing/Disinfecting Solution: | 1.35 parts by weight dry solid formulation | |
| | Water (to make 100 parts by weight) | |

EXAMPLE 39

| Dry Solid Formulation: | Sodium lauryl sulfate | (0.82 wt %) |
| | Citric acid | (33.01 wt %) |
| | Ascorbic acid | (33.01 wt %) |
| | Lauric acid | (0.13 wt %) |
| | Sodium acid pyrophosphate | (33.01 wt %) |
| Sanitizing/Disinfecting Solution: | 3.04 parts by weight dry solid formulation | |
| | Water (to make 100 parts by | |

EXAMPLE 40

| Dry Solid Formulation: | Sodium lauryl sulfate | (0.82 wt %) |
| --- | --- | --- |
| | Citric acid | (33.01 wt %) |
| | Erythrobic acid | (33.01 wt %) |
| | Lauric acid | (0.13 wt %) |
| | Sodium acid pyrophosphate | (33.01 wt %) |
| Sanitizing/ Disinfecting Solution: | 3.04 parts by weight dry solid formulation Water (to make 100 parts by weight) | |

EXAMPLE 41

| Dry Solid Formulation: | Sodium lauryl sulfate | (1.23 wt %) |
| --- | --- | --- |
| | Citric acid | (49.28 wt %) |
| | Ascorbic acid | (49.28 wt %) |
| | Lauric acid | (0.20 wt %) |
| Sanitizing/ Disinfecting Solution: | 2.03 parts by weight dry solid formulation Water (to make 100 parts by weight) | |

EXAMPLE 42

| Dry Solid Formulation: | Sodium lauryl sulfate | (1.23 wt %) |
| --- | --- | --- |
| | Citric acid | (49.28 wt %) |
| | Erythorbic acid | (49.28 wt %) |
| | Lauric acid | (0.20 wt %) |
| Sanitizing/ Disinfecting Solution: | 2.03 parts by weight dry solid formulation Water (to make 100 parts by weight) | |

EXAMPLE 43

| Dry Solid Formulation: | Sodium lauryl sulfate | (0.43 wt %) |
| --- | --- | --- |
| | Citric acid | (13.68 wt %) |
| | Ascorbic acid | (42.91 wt %) |
| | Lauric acid | (0.07 wt %) |
| | Sodium acid pyrophosphate | (42.91 wt %) |
| Sanitizing/ Disinfecting Solution: | 2.33 parts by weight dry solid formulation Water (to make 100 parts by weight) | |

EXAMPLE 44

| Dry Solid Formulation: | Sodium lauryl sulfate | (0.43 wt %) |
| --- | --- | --- |
| | Citric acid | (13.68 wt %) |
| | Erythorbic acid | (42.91 wt %) |
| | Lauric acid | (0.07 wt %) |
| | Sodium acid pyrophosphate | (42.91 wt %) |
| Sanitizing/ Disinfecting Solution: | 2.33 parts by weight dry solid formulation Water (to make 100 parts by weight) | |

EXAMPLE 45

| Dry Solid Formulation: | Sodium lauryl sulfate | (0.75 wt %) |
| --- | --- | --- |
| | Citric acid | (23.91 wt %) |
| | Ascorbic acid | (75.21 wt %) |
| | Lauric acid | (0.12 wt %) |
| Sanitizing/ Disinfecting Solution: | 1.33 parts by weight dry solid formulation Water (to make 100 parts by weight) | |

EXAMPLE 46

| Dry Solid Formulation: | Sodium lauryl sulfate | (0.75 wt %) |
| --- | --- | --- |
| | Citric acid | (23.91 wt %) |
| | Erythorbic acid | (75.21 wt %) |
| | Lauric acid | (0.12 wt %) |
| Sanitizing/ Disinfecting Solution: | 1.33 parts by weight dry solid formulation Water (to make 100 parts by weight) | |

EXAMPLE 47

| Dry Solid Formulation: | Sodium lauryl sulfate | (0.33 wt %) |
| --- | --- | --- |
| | Citric acid | (33.20 wt %) |
| | Ascorbic acid | (33.20 wt %) |
| | Lauric acid | (0.05 wt %) |
| | Sodium acid pyrophosphate | (33.20 wt %) |
| Sanitizing/ Disinfecting Solution: | 3.03 parts by weight dry solid formulation Water (to make 100 parts by weight) | |

EXAMPLE 48

| Dry Solid Formulation: | Sodium lauryl sulfate | (0.33 wt %) |
| --- | --- | --- |
| | Citric acid | (33.20 wt %) |
| | Erythorbic acid | (33.20 wt %) |
| | Lauric acid | (0.05 wt %) |
| | Sodium acid pyrophosphate | (33.20 wt %) |
| Sanitizing/ Disinfecting Solution: | 3.03 parts by weight dry solid formulation Water (to make 100 parts by weight) | |

EXAMPLE 49

| Dry Solid Formulation: | Sodium lauryl sulfate | (0.49 wt %) |
| --- | --- | --- |
| | Citric acid | (49.71 wt %) |
| | Ascorbic acid | (49.71 wt %) |
| | Lauric acid | (0.08 wt %) |
| Sanitizing/ Disinfecting Solution: | 2.03 parts by weight dry solid formulation Water (to make 100 parts by weight) | |

EXAMPLE 50

| Dry Solid Formulation: | Sodium lauryl sulfate | (0.49 wt %) |
| --- | --- | --- |
| | Citric acid | (49.71 wt %) |
| | Erythorbic acid | (49.71 wt %) |
| | Lauric acid | (0.08 wt %) |
| Sanitizing/ Disinfecting | 2.03 parts by weight dry solid formulation | |

-continued

| Solution: | Water (to make 100 parts by weight) |

EXAMPLE 51

| Dry Solid Formulation: | Sodium lauryl sulfate | (0.59 wt %) |
| --- | --- | --- |
| | Erythorbic acid | (23.66 wt %) |
| | Citric acid | (23.66 wt %) |
| | Lauric acid | (0.17 wt %) |
| | Sodium acid pyrophosphate | (49.73 wt %) |
| | Benzoic acid | (2.36 wt %) |
| Sanitizing/ Disinfecting Solution: | 1.7 parts by weight dry solid formulation Water (to make 100 parts by weight) | |

EXAMPLE 52

| Dry Solid Formulation: | Sodium lauryl sulfate | (0.32 wt %) |
| --- | --- | --- |
| | Erythorbic acid | (32.15 wt %) |
| | Citric acid | (32.15 wt %) |
| | Sodium acid pyrophosphate | (32.15 wt %) |
| | Benzoic acid | (3.23 wt %) |
| Sanitizing/ Disinfecting Solution: | 3.12 parts by weight dry solid formulation Water (to make 100 parts by weight) | |

EXAMPLE 53

| Dry Solid Formulation: | Sodium lauryl sulfate | (0.62 wt %) |
| --- | --- | --- |
| | Erythorbic or ascorbic acid | (24.84 wt %) |
| | Citric acid | (24.84 wt %) |
| | Sodium acid pyrophosphate | (49.69 wt %) |
| Sanitizing/ Disinfecting Solution: | 4.03 parts by weight dry solid formulation Water (to make 100 parts by weight) | |

The antimicrobial efficacy of the reconstituted aqueous solutions of the dry salad freshener or sanitizer formulations of Example 31–34 above was evaluated using the procedure of Method No. 6 from the 13th Edition of the *Official Methods of Analysis of the A. O. A. C.*, 1111 North 19th Street, Alexandria, Va. 22209 described above. The results of these tests appear in Table 3.

TABLE 3

MICROBIOLOGICAL EFFICACY OF RECONSTITUTED AQUEOUS SOLUTIONS OF SOLID SALAD FRESHENER/ SANITIZER FORMULATIONS OF THE INVENTION

| | | | Number of Bacteria/mL | | |
| --- | --- | --- | --- | --- | --- |
| Example | Test | Bacterial Species | Initially | After 30 sec. | After 60 sec. |
| 31 | 1 | Staphylococcus aureus | $77 \times 10^6$ | 2 | 0 |
| 31 | 2 | Staphylococcus aureus | $77 \times 10^6$ | 1 | 0 |
| 31 | 3 | Escherichia coli | $79 \times 10^6$ | 0 | 0 |
| 31 | 4 | Escherichia coli | $79 \times 10^6$ | 0 | 0 |
| 32 | 1 | Staphylococcus aureus | $77 \times 10^6$ | 6 | 0 |
| 32 | 2 | Staphylococcus aureus | $77 \times 10^6$ | 0 | 0 |
| 32 | 3 | Escherichia coli | $79 \times 10^6$ | 0 | 0 |
| 32 | 4 | Escherichia coli | $79 \times 10^6$ | 0 | 0 |
| 33 | 1 | Staphylococcus aureus | $77 \times 10^6$ | 0 | 0 |
| 33 | 2 | Staphylococcus aureus | $77 \times 10^6$ | 0 | 0 |
| 33 | 3 | Escherichia coli | $79 \times 10^6$ | 0 | 0 |
| 33 | 4 | Escherichia coli | $79 \times 10^6$ | 0 | 0 |
| 34 | 1 | Staphyloccoccus aureus | $77 \times 10^6$ | 2 | 0 |
| 34 | 2 | Staphylococcus aureus | $77 \times 10^6$ | 0 | 0 |
| 34 | 3 | Escherichia coli | $79 \times 10^6$ | 0 | 0 |
| 34 | 4 | Escherichia coli | $79 \times 10^6$ | 0 | 0 |

EXAMPLE 54

Determination of Minimum Inhibitory Activities of Igepon AC-78 and Lathanol LAL Against *Staphylococcus aureus* and *Escherichia coli*

Concentrated aqueous stock solutions of Igepon AC-78 and Lathanol LAL were prepared to give 30,000 ppm of the active ingredient as follows: 3.6 g of Igepon AC-78 (83% active) and 4.6 g of Lathanol LAL (65% active) were separately dissolved in 100 ml of deionized water and sterilized by membrane filtration. The stock solutions were used for determining the minimum inhibitory concentration against gram positive and gram negative microorganisms represented by *Staphylococcus aureus* ATCC 6538 and *Escherichia coli* ATCC 11229.

The test material was serially two-fold diluted with 5 ml of TSB (tryptic soy broth). The dilutions were innoculated with 0.1 ml of 1/100 dilution of 24 hr old bacteria culture growth in TSB at 37° C. The innoculated tubes were incubated at 37° C. and the results were read after 24 and 48 hours. Appearance of turbidity was recorded as microbial growth. The tubes with Igepon AC-78 had initial turbidity. A loopful was plated on plate count agar to differentiate between turbidity of the chemical and microbial growth. The results are presented in Tables 4 and 5.

TABLE 4

MINIMUM INHIBITORY CONCENTRATION OF LATHANOL LAL

| | Time of | ppm | | | | |
| --- | --- | --- | --- | --- | --- | --- |
| Microrg. | Incub. | 250 | 125 | 62.5 | 31.25 | 16.125 |
| S. aureus | 24 hr | — | — | — | + | + |
| | 48 hr | —* | —* | + | + | + |
| E. coli | 24 hr | + | + | + | + | + |
| | 48 hr | + | + | + | + | + |

\* = showed scanty growth when plated.
S. aureus = Staphylococcus aureus
E. coli = Escherichia coli
(−) = no growth
(+) = growth

TABLE 5

MINIMUM INHIBITORY CONCENTRATION OF IGEPON AC-78

| Microrg. | Time of Incub. | 250 ppm | 125 | 62.5 | 31.25 | 16.125 |
|---|---|---|---|---|---|---|
| S. aureus | 24 hr | ± | ± | + | + | + |
|  | 48 hr | + | + | + | + | + |
| E. coli | 24 hr | + | + | + | + | + |
|  | 48 hr | + | + | + | + | + |

S. aureus = Staphylococcus aureus.
E. coli = Escherichia coli
(±) = partial inhibition
(+) = growth

EXAMPLE 55

Determination of Microbicidal Activity

Microbicidal activities of the test compounds were evaluated by the germicidal and detergent sanitizer evaluation method recommended by the association of analytical chemists (A. O. A. C.). It is essentially a suspension test method where a known concentration of the test compound is mixed with a standard suspension of microbial cells. The test was carried out at 25° C. An aliquot of the test mixture is transferred to neutralizing solution at 30 and 60 seconds respectively to stop the action of the test compound and the surviving number of cells are counted by plating on a nutrient medium incubated for 48 hours at 37° C. The test was carried out using S. aureus ATCC 6538 and E. coli ATCC 11229 representing Gram positive and Gram negative bacterial groups.

The test compounds were formulated with citric acid and sodium sulfate. The formulation contained 1.85% Igepon AC-78, 16.27% citric acid and 81.88% sodium sulfate or 2.35% Lanthanol LAL, 16.19% citric acid and 81.46% sodium sulfate. In the test either 1.96 g of Lathanol or 1.95 g of Igepon preparation per 100 ml of test volume were used resulting in 300 ppm of active compounds in the final test. The results are presented in the following Table 6.

TABLE 6

BACTERICIDAL ACTIVITY OF IGEPON AC-78 AND LATHANOL LAL

| | | No. of surviving cells after contact time in seconds | | | |
|---|---|---|---|---|---|
| | | S. aureus | | E. coli | |
| Compound | ppm | 30 | 60 | 30 | 60 |
| Lathanol LAL | 300 | 28, 36 | 0, 0 | T, T | T, T |
| % Kill | | >99.999 | >99.999 | ND, ND | ND, ND |
| Igepon AC-78 | 300 | 190,176 | 8, 5 | 25, 25 | 0, 0 |
| % Kill | | >99.999 | >99.999 | >99.999 | >99.999 |
| Hypochlorite | 50 | 0, 0 | 0, 0 | 0, 0 | 0, 0 |
| Control | — | 117 million | | 110 million | |

T = too numerous to count
ND = not determined
0 = no growth

EXAMPLE 56

Effect Of pH On The Ranoe Of Microbicidal Activity

The test compounds were prepared in citrate-phosphate buffer with pH values ranging from 2.5 to 5.0 with 0.5 incremental values. One ml of the stock solution containing 300 ppm of the active material was added to the 100 ml of the buffer solution for testing the activity at a desired pH. The sanitizer tests were carried out as described earlier in Example 2. The results are presented in Tables 7 and 8.

TABLE 7

EFFECT OF pH ON BACTERICIDAL ACTIVITY OF IGEPON AC-78

| | | No. of surviving cells after contact time in seconds | | | |
|---|---|---|---|---|---|
| | | S. aureus | | E. coli | |
| Compound | ppm | 30 | 60 | 30 | 60 |
| IGEPON AC-78 | | | | | |
| pH 2.5 | 300 | *13, 8 | 1, 0 | 0, 0 | 0, 0 |
| % Kill | | >99.999 | >99.999 | >99.999 | >99.999 |
| pH 3.0 | 300 | T, T | T, T | 0, 0 | 0, 0 |
| % Kill | | ND, ND | ND, ND | >99.999 | >99.999 |
| pH 3.5 | 300 | T, T | T, T | T, T | 0, 0 |
| % Kill | | ND, ND | ND, ND | ND, ND | >99.999 |
| pH 4.0 | 300 | T, T | T, T | T, T | T, T |
| % Kill | | ND, ND | ND, ND | ND, ND | ND, ND |
| pH 4.5 | 300 | T, T | T, T | T, T | T, T |
| % Kill | | ND, ND | ND, ND | ND, ND | ND, ND |
| pH 5.0 | 300 | T, T | T, T | T, T | T, T |
| % Kill | | ND, ND | ND, ND | ND, ND | ND, ND |
| Hypochlorite | 50 | 0, 0 | 0, 0 | 0, 0 | 0, 0 |
| Control | — | 112 million | | 93 million | |

T = too numerous to count
ND = not determined
* = number of cells
0 = no growth

TABLE 8

EFFECT OF pH ON BACTERICIDAL ACTIVITY OF LATHANOL LAL

| | | No. of surviving cells after contact time in seconds | | | |
|---|---|---|---|---|---|
| | | S. aureus | | E. coli | |
| Compound | ppm | 30 | 60 | 30 | 60 |
| LAL LATHANOL LAL | | | | | |
| pH 2.5 | 300 | 0, 0 | 0, 0 | 0, 0 | 0, 0 |
| % Kill | | >99.999 | >99.999 | >99.999 | >99.999 |
| pH 3.0 | 300 | *79, 99 | 0, 6 | 0, 0 | 0, 0 |
| % Kill | | >99.999 | >99.999 | >99.999 | >99.999 |
| pH 3.5 | 300 | 129,161 | 13, 14 | T, T | T, T |
| % Kill | | >99.998 | >99.999 | >99.999 | >99.999 |
| pH 4.0 | 300 | T, T | T, T | T, T | T, T |
| % Kill | | ND, ND | ND, ND | ND, ND | ND, ND |
| pH 4.5 | 300 | T, T | T, T | T, T | T, T |
| % Kill | | ND, ND | ND, ND | ND, ND | ND, ND |
| pH 5.0 | 300 | T, T | T, T | T, T | T, T |
| % Kill | | ND, ND | ND, ND | ND, ND | ND, ND |
| Hypochlorite | 50 | 0, 0 | 0, 0 | 0, 0 | 0, 0 |
| Control | — | 112 million | | 93 million | |

T = too numerous to count
ND = not determined
* = number of cells
0 = no growth

EXAMPLE 57

Powder Concentrate Anti-Protozoal Preparation

| Composition A: | |
|---|---|
| Sodium lauryl sulfate | 7.27% |
| Citric acid | 92.72% |

Use 0.3437 gm of composition A per 100 ml water.

EXAMPLE 58

Use Level Aqueous Anti-Protozoal Preparation

| Composition B (liquid preparation): | |
|---|---|
| Sodium lauryl sulfate | 0.025% |
| Citric acid | 0.154% |
| Deionized water | 100.0 ml |

EXAMPLE 59

Concentrated Nonaqueous Anti-Protozoal Preparation

| Composition C: | |
|---|---|
| Sodium lauryl sulfate | 4.0% |
| Citric acid (Anhydrous) | 29.0% |
| Propylene glycol | 67.0% |

EXAMPLE 60

Anti-Protozoal Lotion

| Composition D: | |
|---|---|
| Sodium lauryl sulfate | 0.30% |
| Citric acid (Anhydrous) | 0.16% |

| Composition D: | |
|---|---|
| Propylene glycol | 99.81% |

For direct use as lotion.

One ml of *Giardia muris* cysts suspension was mixed with 9 ml of test preparations and allowed to react for 15 and 30 minutes in a conical centrifuge tube at 25° C. At the end of the treatment the mixture was centrifuged at 650 g for 2 minutes to remove the test preparation as supernatant and the pelleted cysts were washed by suspending in 10 ml of reducing solution as described by Sauch in Advances in Giardia Research, p. 261–264, 1988, University of Calgary Press, Canada. The cysts were then subjected to excystation procedure as described by Sauch. Cysts suspension which did not undergo excystation treatment served as negative control while cyst suspension without any cysticidal treatment that was subjected to excystation served as positive control. The unexcysted cysts were counted under microscope by using haemcytometer. The number of cysts that remained unexcysted in controls were considered as not viable and the total initial number of cysts was reduced by this FIGURE to calculate the percentage killed by the chemical treatment. The results are tabulated and are presented in Tables 9, 10 and 11 as follows:

TABLE 9

VIABILITY OF GIARDIA CYSTS AFTER 30-MINUTE TREATMENT WITH COMPOSITION A

| | | No. of cysts per ml (× 10,000) | | | | |
|---|---|---|---|---|---|---|
| | | Control | | | Test | |
| Chemical | ppm | Before *Excyst. | After *Excyst. | Excysted | After *Excyst. | % Killed |
| Untreated Control | — | 43 | 4[a] | 90.6 | — | — |
| COMPOSITION A | | | | | | |
| SDS + | 250 | | | | | |
| Citric acid | 3187 | (43)[b] | — | — | 40 | 93.0 |

SDS = Sodium lauryl sulfate
ppm = parts per million
* = Excystation
[a] = Unexcysted cysts
[b] = Not corrected for unexcysted cysts in control

TABLE 10

EFFECT OF 15-CONTACT TIME WITH COMPOSITION A AND B ON SURVIVAL OF GIARDIA CYSTS

| | | No. of cysts per ml (× 10,000) | | | | |
|---|---|---|---|---|---|---|
| | | Control | | | Test | |
| Chemical | ppm | Before *Excyst. | After *Excyst. | Excysted | After *Excyst. | % Killed |
| Untreated Control | — | 274 | 0 | 100 | — | — |
| COMPOSITION A | | | | | | |
| SDS + | 250 | | | | | |
| Citric acid | 3187 | (274) | — | — | 265 | 96.7 |
| COMPOSITION B | | | | | | |
| SDS + | 250 | | | | | |
| Citric acid | 1540 | (274) | — | — | 271 | 98.9 |
| SDS (control) | 250 | (274) | — | — | 1 | 0.3 |
| Citric acid | 3187 | (274) | — | — | 2 | 0.7 |

TABLE 10-continued

EFFECT OF 15-CONTACT TIME WITH COMPOSITION A AND B ON SURVIVAL OF GIARDIA CYSTS

| | | No. of cysts per ml (× 10,000) | | | | |
|---|---|---|---|---|---|---|
| | | Control | | | Test | |
| Chemical | ppm | Before *Excyst. | After *Excyst. | Excysted | After *Excyst. | % Killed |
| (control) | | | | | | |

SDS = Sodium lauryl sulfate
ppm = parts per million
* = Excystation

TABLE 11

EFFECT OF 30-CONTACT TIME WITH COMPOSITIONS A AND B ON SURVIVAL OF GIARDIA CYSTS

| | | No. of cysts per ml (10,000) | | | | |
|---|---|---|---|---|---|---|
| | | Control | | | Test | |
| Chemical | ppm | Before *Excyst. | After *Excyst. | Excysted | After *Excyst. | % Killed |
| Untreated Control | — | 274 | 3$^a$ | 98.9 | — | — |
| COMPOSITION A | | | | | | |
| SDS | 250 | | | | | |
| + | | | | | | |
| Citric acid | 3187 | (27)$^b$ | — | — | 255 | 93.0 |
| COMPOSITION B | | | | | | |
| SDS | 250 | | | | | |
| + | | | | | | |
| Citric acid | 1540 | (27)$^b$ | — | — | 227 | 83.8 |
| SDS (control) | 250 | (271)$^b$ | — | — | 3 | 1.1 |
| Citric acid (control) | 3187 | (271)$^b$ | — | — | 0 | 0 |

SDS = Sodium lauryl sulfate
ppm = parts per million
* = Excystation
$a$ = Unexcysted cysts
$b$ = Not corrected for unexcysted cysts in control The foregoing examples in Tables 9, 10 and 11 illustrate that the compositions are capable of reducing the number of giardial cysts by approximately 82% to 92% in 15- or 30-minute treatments. Thus, the compositions can be used against protozoal cysts that survive outside the host in adverse conditions and transmit infections. The cysticidal preparations of the present invention can be used a variety of conditions to kill the infective agent.

The examples presented above are merely illustrative and should not be read as limiting the scope of the invention as it is defined in the appended claims.

I claim:

1. In the art of disinfecting and sanitizing contamination with cyst or oocyte forms of protozoa resistant to (a) anionic surfactants diluted in water alone, or (b) a below pH 5.0 producing acidic component diluted in water alone, the improvement consisting essentially of the step of contacting said protozoa cyst or oocyte resistant forms with an aqueous solution of a) and b) prepared from an anhydrous liquid or dry powdered concentrate diluted with water.

* * * * *

UNITED STATES PATENT AND TRADEMARK OFFICE
CERTIFICATE OF CORRECTION

PATENT NO. : 5,280,042

DATED : January 18, 1994

INVENTOR(S) : Lopes

It is certified that error appears in the above-identified patent and that said Letters Patent is hereby corrected as shown below:

Column 1, line 28, delete "onocarboxylic" and insert --monocarboxylic--;

Column 6, line 17, delete "tee" and insert --the--;

Column 8, line 9, delete "ca" and insert --can--;

Column 11, line 19, delete "Example __" and insert --Example 13--;

Column 14, line 65, delete "lll" and insert --llll--;

Column 23, line 61, delete "Ranoe" and insert --Range--.

Signed and Sealed this

Nineteenth Day of July, 1994

BRUCE LEHMAN

Attest:

Attesting Officer

Commissioner of Patents and Trademarks